(12) United States Patent
Russell

(10) Patent No.: US 10,398,643 B2
(45) Date of Patent: *Sep. 3, 2019

(54) TRANSDERMAL ADMINISTRATION OF ANTIOXIDANT FOR TREATMENT OF PAIN AND INFLAMMATION

(71) Applicant: Kenneth Russell, Austin, TX (US)

(72) Inventor: Kenneth Russell, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/925,437

(22) Filed: Mar. 19, 2018

(65) Prior Publication Data

US 2018/0221273 A1    Aug. 9, 2018

Related U.S. Application Data

(63) Continuation-in-part of application No. 15/154,671, filed on May 13, 2016, now Pat. No. 10,172,847.

(51) Int. Cl.
| | |
|---|---|
| *A61K 31/4704* | (2006.01) |
| *A61K 31/4196* | (2006.01) |
| *A61K 31/4045* | (2006.01) |
| *A61K 31/164* | (2006.01) |
| *A61K 31/4412* | (2006.01) |
| *A61K 31/426* | (2006.01) |
| *A61K 31/198* | (2006.01) |
| *A61K 9/00* | (2006.01) |
| *A61P 25/00* | (2006.01) |
| *A61P 29/00* | (2006.01) |
| *A61K 9/06* | (2006.01) |
| *A61K 33/30* | (2006.01) |
| *A61K 38/20* | (2006.01) |
| *A61K 31/616* | (2006.01) |
| *A61K 31/6615* | (2006.01) |
| *A61K 31/16* | (2006.01) |
| *A61K 9/08* | (2006.01) |
| *A61K 9/12* | (2006.01) |

(52) U.S. Cl.
CPC .......... *A61K 9/0019* (2013.01); *A61K 9/0014* (2013.01); *A61K 9/06* (2013.01); *A61K 31/16* (2013.01); *A61K 31/198* (2013.01); *A61K 31/4045* (2013.01); *A61K 31/4196* (2013.01); *A61K 31/4412* (2013.01); *A61K 31/616* (2013.01); *A61K 31/6615* (2013.01); *A61K 33/30* (2013.01); *A61K 38/2066* (2013.01); *A61P 25/00* (2018.01); *A61P 29/00* (2018.01); *A61K 9/08* (2013.01); *A61K 9/12* (2013.01)

(58) Field of Classification Search
CPC ............ A61K 31/4704; A61K 31/4412; A61K 31/426; A61K 31/4196; A61K 31/198; A61K 31/164; A61K 31/4045

See application file for complete search history.

(56) References Cited

U.S. PATENT DOCUMENTS

| | | | | |
|---|---|---|---|---|
| 5,518,960 | A * | 5/1996 | Tsuchimoto | ...... H01L 21/76838 257/E21.582 |
| 6,899,667 | B2 * | 5/2005 | Becker | .................. A61N 2/008 336/122 |
| 8,309,081 | B2 * | 11/2012 | Studin | .................... A61K 36/15 424/94.65 |

* cited by examiner

*Primary Examiner* — Jennifer M Kim

(74) *Attorney, Agent, or Firm* — Pham IP Group; Frank H. Pham

(57) ABSTRACT

Methods and compositions for the treatment of pain associated with inflammation in a patient by transdermal delivery of antioxidant to increase glucose uptake and anti-inflammatory cytokines that act to reduce pain.

4 Claims, No Drawings

TRANSDERMAL ADMINISTRATION OF ANTIOXIDANT FOR TREATMENT OF PAIN AND INFLAMMATION

CROSS-REFERENCE TO RELATED APPLICATION

This application is a continuation-in-part of U.S. Non-provisional application Ser. No. 15/154,671 filed on May 13, 2016. All the foregoing applications are incorporated herein by reference in their entireties.

BACKGROUND OF THE DISCLOSURE

1. Field of the Invention

The present invention relates to methods and compositions for the treatment of pain associated with inflammation in a patient. Particularly, the present invention pertains to a transdermal delivery of antioxidant compositions to increase glucose uptake and anti-inflammatory cytokines that act to reduce pain at inflammatory tissues.

2. Description of the Prior Art

Inflammation is a biological response that can result from a noxious stimulus and is normally intended to remove that stimulus or ameliorate its effects. Although normally intended to promote survival, inflammation can cause damage to the host.

Cytokines play an important role in the initiation and maintenance of inflammatory diseases as mediators of cell-cell interactions. In addition to their enhancing and inhibitory effects on immune and inflammatory cells, cytokines exert considerable influence over sensory neurones. Cytokines may act directly on nociceptors or, more commonly, indirectly, stimulating the release of agents such as prostaglandins. During acute phases, cytokines appear to induce sensitization via receptor-associated kinases and phosphorylation of ion channels whereas in chronic inflammation transcriptional up-regulation of receptors and secondary signaling become more important.

Inflammation and pain can be determined in number of ways. Determinations can be made by measuring IL-1β and transforming growth factor levels (TGF) wherein an increase in either or both factors correspond to a decrease in anti-inflammatory cytokine activity.

The anti-inflammatory cytokines are a series of immunoregulatory molecules that control the pro-inflammatory cytokine response. Cytokines act in concert with specific cytokine inhibitors and soluble cytokine receptors to regulate the human immune response. Their physiologic role in inflammation and pathologic role in systemic inflammatory states are increasingly recognized. Major anti-inflammatory cytokines include interleukin (IL)-1 receptor antagonist, IL-4, IL-10, IL-11, and IL-13. Leukemia inhibitory factor, interferon-alpha, IL-6, and transforming growth factor (TGF)-β are categorized as either anti-inflammatory or pro-inflammatory cytokines, under various circumstances. Specific cytokine receptors for IL-1, TNF-α, and IL-18 also function as inhibitors for pro-inflammatory cytokines.

Pro-inflammatory cytokines are produced predominantly by activated macrophages and are involved in the up-regulation of inflammatory reactions. Macrophages maintain sufficient supply of iron for erythropoiesis and an increase of IL-1beta promotes efficient iron storage within macrophages or monocytes by increasing the expression of ferritin, both at the transcriptional and posttranscriptional level.

Certain inflammatory cytokines are also involved in nerve-injury/inflammation-induced central sensitization, and are related to the development of contralateral hyperalgesia/allodynia. The discussion presented in the present invention describes several key pro-inflammatory cytokines and anti-inflammatory cytokines, their relation with pathological pain in human patients, and possible underlying mechanisms.

Independently of the inducing factor—and the length of the exposure—an inflammatory reaction is mediated by a varied number and type of cells and molecules, the later including cytokines, growth factors, clotting factors, enzymes, neurotransmitters and complement proteins, among others. These molecules are primarily secreted by fibroblasts, endothelial and infiltrating cells (e.g. macrophages, lymphocytes, mast cells, polymorphonuclear cells, etc), and local nerves in response to the insulting agent. The mixture and amount of cytokines therein released will depend on the type, concentration and exposure time of the inducing agent. Therefore, these proteins could mediate from an acute local inflammatory reaction to systemic life-threatening responses (e.g. acute systemic inflammatory response syndrome, SIRS; multiple organ failure as in septic shock; anaphylaxis, etc).

In chronic inflammatory processes, the cytokines continuously recruit more and more infiltrating cells that generate, for example, granulomas, induration of the tissues, and encapsulated abscesses. In any case, proteins secreted during an inflammatory process are central players in the grade and persistence of the final reaction.

Cytokines produce during acute inflammation can be divided into two group: pro-inflammatory cytokines (eg, IL-1 and TNF-α) and anti-inflammatory cytokines (eg, IL-4). Inflammation also draws phatocytes to the site of pathogen invasion, where the phagocytes generally efficiently recognize, ingest, and kill the extracellular pathogens.

Cytokines are critical mediators of protective host responses, including defense against microbial invasion and tumorigenesis. However, the production of specific pro-inflammatory cytokines must be tightly regulated and compartmentalized to prevent the overzealous expression of these molecules that can culminate in unabated inflammation and tissue injury. Cytokine production and/or biologic effects can be inhibited by a variety of endogenous molecules, including anti-inflammatory cytokines, soluble cytokine receptors, and receptor antagonist proteins. Additionally, synthetic molecules have been constructed to selectively block the synthesis, post-translation processing, or receptor binding of pro-inflammatory cytokines. Relevant anti-inflammatory cytokines and cytokine inhibitors (both endogenous and synthetic) will be the subject of this review, with a particular emphasis on those anti-inflammatory cytokines and cytokine inhibitors that have been used experimentally or clinically in the treatment of diseases that are believed to be mediated by excessive pro-inflammatory cytokine responses.

Recent studies show that when macrophages are activated by cytokine IL-17, which is a product of effector CD4 Th17 lymphocytes, they secrete oxidative radicals in their microenvironment, which can kill bacteria and destroy viruses. Activated macrophages further help the renewal of tissue integrity (wound healing) by secreting various cytokines and chemokines. Killing bacteria can also take place intracellularly, after macrophages become activated with IFN-y (because some bacteria can live inside cells, such as those belonging to *mycrobacteria, salmonella,* or *leishmanial*). Macrophages secrete pro-inflammatory cytokines (IL-1β and TNF-α), chemotactic cytokines (chemokines such as IL-8=CXCL8), regulatory cytokines including pro-inflammatory IL-1, IL-6, IL-12 and TNF-α, when activated, but also anti-inflammatory cytokines, such as IL-10 and TGB-β in non-activated state. (Zlatko et. Al., 2015).

Inflammation can also be determined by the concentration of iron at an inflammatory site. High iron concentration may amplify the damaging effects of superoxide overproduction in a very broad spectrum of inflammatory, both acute and chronic conditions.

Iron overload may amplify the damaging effects of superoxide overproduction in a very broad spectrum of inflammatory, both acute and chronic, conditions. Furthermore, chronic oxidative stress may modulate iron uptake and storage, leading to a self-sustained and ever increasing spiral of cytotoxic and mutagenic events.

Researches have shown that increases in the rate and volume of glucose and amino acid maturing M1 macrophages increases the rate and volume of intracellular mitochondrial ATP formation, glutathione formation, ferritin formation for safe iron storage, and the transferrin receptor formation for accelerated iron uptake. This increases the rate and volume of inflammatory iron uptake into M1 macrophages (insulin mediated transferrin bound iron uptake) and safe sequestration into maturing M1 macrophages. Accelerated iron uptake into M1 macrophages shortens the damage from inflammatory iron, shortens the term of secretion of inflammatory cytokines by M1 macrophages, shortens the delay in the secretion of anti-inflammatory cytokines by transitioning M1 to M2 macrophages.

M1 macrophages begin transition to M2 macrophages as they become maximally iron loaded and they reduce their secretion of inflammatory cytokines.

Immature/non-polarized macrophages initially become trapped at an inflammation site (inflammatory iron reduces vasodilation and microvascular throughput) as immature and non-polarized macrophages initiate polarization toward M1 status and the distribution of inflammatory cytokines.

Many substances are applied topically to the skin or mucous membranes of humans or animals (hereinafter "skin") to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Many topical formulations contain chemical emulsions which use surface active ingredients (emulsifiers) to disperse dissimilar chemicals in a particularly solvent system. For example, most lipid-like (oily or fatty) or lipophilic ingredients do not uniformly disperse in aqueous solvents unless they are first combined with emulsifiers which form microscopic aqueous soluble micelles that contain a lipid-soluble interior and an aqueous-soluble exterior, resulting in an oil-in-water emulsion. To be soluble in aqueous media, a molecule must be polar or charged so that to favorably interact with water molecules which are also polar. Similarly, to dissolve an aqueous-soluble polar or charged ingredient in a largely lipid or oil-based solvent, an emulsifier is typically used which forms stable micelles that contain the aqueous soluble components in the micelle interior while the exterior of the micelle is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion micelle. Emulsion destabilization results in the aqueous and lipophilic ingredients separating into two layers, potentially destroying the commercial value of a topical product. Because the aqueous-soluble strontium cation has two positive charges, it is especially disruptive of emulsion systems compared to ions with only one positive charge (e.g., sodium ions). The concentrations of strontium salts, particularly strontium nitrate, in many of the topical formulations of the present invention that provide an optimum consumer benefit (e.g., anti-irritant properties) are approximately 4-6% 35 w/w (approximately 190-280 mM). In this concentration range many common emulsion systems become unstable and separate into their two phases. The formulations of the invention have overcome the inherent tendency of high salt concentrations in general, and high strontium salt concentrations to destabilize emulsions.

Accordingly, it is desirable to identify methods and compositions which are effective in the skin to remove iron concentration at the inflammatory tissues while not adversely damaging the tissues. Furthermore, there is a need to increase anti-inflammatory cytokines to kill bacteria intracellularly, which may cause skin infections.

Thus, an aspect of the present invention is to provide transdermal product formulations that comprise an antioxidant composition at an effective amount to reduce pain associated with inflammation.

SUMMARY OF THE DISCLOSURE

The present invention is based on a discovery that reduces pain by transdermally delivering antioxidant to increase glucose uptake and anti-inflammatory cytokines, such as IL-10 targeting cells and tissues.

In particularly, the invention has shown in pain models that a novel therapy of transdermal delivery of antioxidant composition to increase glucose uptake and anti-inflammatory cytokines and pro-inflammatory cytokine antagonists to prevent and reverse pain, such as pathological and neuropathic pain, including thermal hyperalgesia and mechanical allodynia, without affecting basal pain responsivity to thermal or mechanical stimuli.

In one embodiment, transdermally administering the antioxidant composition increases the rate and volume of iron uptake into the maturing M1 macrophage by optimizing insulin mediated uptake transferrin bound iron, glucose and amino acids.

In another embodiment, administering the antioxidant composition reduces the ATP cost and the time expenditure of endogenously produced antioxidants and iron regulatory proteins. When the maximal levels of inflammatory iron have been absorbed into M1 macrophages and the restoration of microvascular throughput has been achieved (reduced levels of labile inflammatory iron), iron loaded M1 macrophages are no longer trapped within the microvascular impairment of the inflamed tissues. Fully iron loaded and polarized M1 macrophages cease the dumping of inflammatory cytokines and begin to transition into M2 macrophages status. When transitioning M2 macrophages encounter the correct signaling from micro environments in the liver, spleen, and bone marrow they will dump significant amounts of iron into those tissues to redistribute iron for the formation of red blood cells. Therefore, mature M2 macrophages that become trapped in iron loaded and microvascular impaired tissues will begin to load iron and transition back towards M1 macrophage polarization.

In another embodiment, the antioxidant composition inhibits products of glial activation that lead to pathology while leaving basal glial and neuronal functions unaltered, this novel therapy approach for the reduction of pain provides a highly desirable alternative to neuronally focused therapies such as opioid drugs. Moreover, IL-10 and other agents that act on pro-inflammatory cytokines can be delivered either alone or in conjunction with the antioxidant composition to treat existing pain.

In one embodiment, the invention is directed to a method of treating pain, such as neuropathic pain, in a patient comprising transdermally administering at five days or less an antioxidant composition comprising active ingredients selected from the group consisting of an anti-inflammatory cytokine, a pro-inflammatory cytokine antagonist, and an agent that acts to reduce or prevent pro-inflammatory cytokine actions, operably linked to expression control elements, under conditions that result in expression of the polynucleotide in vivo to reduce pain.

In additional embodiments, the invention is directed to a method of treating existing pain in a patient, such as neuropathic pain, comprising administering to the subject a therapeutically effective amount of a composition comprising an IL-10 polypeptide. In certain embodiments, the IL-10 polypeptide is fused to the Fc portion of an IgG. In additional embodiments, the anti-inflammatory cytokine is human IL-10.

In another embodiment, the present invention provides a Macrophage Activating Agent (MAA), more particularly a composition comprising at least a Macrophage Activating Agent (MAA), for use in the treatment of pain and inflammation in a patient and for the treatment and prevention of symptoms thereof. Indeed, the present inventors have found that administration of a MAA, leads to a significant decrease of the manifestation of the symptoms of endometriosis, without causing significant side effects. In certain embodiments, the composition is used for reducing one or more signs or symptoms of endometriosis selected from the group consisting of pelvic pain, dysmenorrhoea, dyspareunia, dysuria, irregular menstruation, amenorrhoea, pre-menstrual syndrome, abdominal pain, fatigue, infertility, and constipation.

A preferred embodiment of the present invention includes administering the antioxidant composition in conjunction with one or more therapeutic agents, e.g., one or more compositions selected from the group consisting of anti-viral agents, anti-inflammatory agents, and combinations thereof. Administering such therapeutic agents in conjunction with the iron composition includes administering one or more of such agents, e.g., prior to, during (e.g., contemporaneously, by co-administration or in combination with), or following administration of the composition.

A preferred embodiment of the present invention providing the administration of the antioxidant composition to a cutaneous site of inflammation or potential inflammation. The administration of the composition can be in conjunction with transdermal formulations applied directly to the cutaneous site.

A preferred embodiment of the present invention is directed to transdermal formulations as a delivery vehicle containing the lipophilic, hydrophilic and surfactant components and aqueous oil based solution thereof as ingredients to provide fast, efficient, and safe topical skin penetration through the stratum corneum of human skin.

A preferred embodiment of the present invention is further directed to one object of the present invention to provide the topical transdermal formulations and ingredients in emulsions which can suppress skin irritation due to tissue inflammation. However, the invention is particularly useful for reducing, inhibiting, and eliminating the inflammation and pain caused by the increase of macrophage iron at the site of the injury or bacterial infection.

A preferred embodiment of the present invention further provides vehicles and vehicle components that are especially useful in the transdermal formulations, as well as concentration ranges and processing steps to obtain useful formulation forms including solids, creams, lotions, gels, and liquids.

The present invention further provides objects and advantages that will become apparent from a description of the several embodiments as set forth in the following description.

DETAILED DESCRIPTION

The method of the present invention provides a method of relieving pain associated with inflammation in a patient, which method comprises administering to the patient an effective amount if therapeutically composition.

The method of the present invention can be used for reducing, inhibiting, and eliminating (e.g., inhibiting the onset of, inhibiting the escalation of, decreasing the likelihood of acute inflammation and chronic inflammation). The inflammation treatable or preventable in accordance with the method of the present invention can include inflammation that results from, e.g., contact with a noxious stimulus, injury, infection, autoimmune reaction, and allergic reaction, including allergic reactions associated with cellular histamine and pro-inflammatory cytokine release.

Studies have suggested that immunologic factors may play a role in the pathogenesis of endometriosis and endometriosis-associated infertility. However, the use of transdermal antioxidant for the treatment of pain associated with inflammation has not been suggested. The present inventors surprisingly found that use of antioxidant composition in patients suffering from pain caused by bacterial infection leads to significant reduction of at least some of the symptoms of pain, without significant side effects. Moreover, in contrast with classic treatments of opioid drugs which attempt to minimize the pain targeting neuronal therapies, treatment with the transdermal antioxidant composition of the present invention does not interfere with the neurotransmitter system.

The present invention found that administration of the antioxidant composition described herein to a patient diagnosed with pain associated with inflammation may result in mitigation of one or more signs and/or symptoms of inflammatory tissues. In further embodiments, these signs and/or symptoms are selected from the group consisting of (chronic) pelvic pain, dysmenorrhea, dyspareunia, dysuria, irregular menstruation, amenorrhoea, pre-menstrual syndrome, abdominal pain, (chronic) fatigue, infertility, and constipation. In further embodiment, the invention relates to the use of the antioxidant compositions described herein for the treatment of amenorrhoea and/abdominal pain (such as dysmenorrheal), more particularly in patients with endometriosis.

The method of the present invention providing the administration of the composition can be in combination with one or more further therapeutic agents and includes simultaneous (concurrent) and consecutive administration in any order. The regulation or administration of the composition can occur after induction of inflammation or pain, but preferably occurs simultaneously with induction of inflammation and pain. The induction of inflammation and/or pain can be the result of sports-related activities, hard labor, blister, repetitive trauma inducing activities or the undertaking of surgery.

The method of the present invention providing the administration of the composition can also be administered to an individual having rheumatoid arthritis to reduce swelling and pain associated with arthritis. Generally, inflammatory disorders include any disorder or condition associated with inflammation, i.e., inflammation of the bowel or any other organ, chemically induced inflammation, inflammation due to repetitive trauma. Each of these conditions, disorders, injuries or inflictions is encompassed by the phase insult resulting in inflammation or pain.

The method of the present invention providing the administration of the composition further comprises at least one antioxidant wherein the antioxidant is selected from the group comprising melatonin, aspirin, IP6, zinc, or combinations thereof.

The method of the present invention providing the administration of the antioxidant composition, via transdermal formations, increases macrophage iron sequestration and iron relocation to be utilized in red blood cell formations. In an embodiment herein, the macrophage iron sequestration is decreased as it is seen in a normal individual in response to an inflammatory stimulus.

The method of the present invention providing the administration of the antioxidant composition applies in anticipation of pain, independent of an inflammatory inducing agent. In this embodiment, thermal sensitivity measured in withdrawal time can be reduced.

The method of the present invention providing the transdermal administration of the antioxidant composition wherein the composition can be formulated according known methods to prepare pharmaceutically useful compositions. By way of example, the pharmaceutical compositions can be formed by combining composition in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of aqueous oil based solutions.

The method of the present invention providing the administration of the antioxidant composition further provides acceptable carriers, excipients or stabilizers are nontoxic to recipients at the dosages and concentrations employed, and include buffers such as antioxidants including ascorbic acid; low molecular weight (less than about 10 residues) polypeptides; hydrophilic polymers such as polyvinyl pyrrolidone, and/or nonionic surfactants such as Tween, Pluronics or PEG. Transdermal formulations are particularly preferred for an efficient and quick delivery method of active agent to targeted location system locally or systematically.

The method of the present invention providing the administration of the antioxidant composition wherein dosages and desired drug concentrations of pharmaceutical compositions of the present invention may vary depending on the particular use envisioned. The determination of the appropriate dosage or route of administration is well within the skill of an ordinary physician.

The method of the present invention providing the administration of the antioxidant composition wherein modulators that enhance the anti-inflammatory and pain reduction activity of cytokine can be identified and administered to an individual in need thereof. The modulation is a change of about at least 10-30%, preferably 40-50%, more preferably at least 50-75%, or most preferably, at least 75-100%. As discussed herein, changes in cytokine activities can be determined by identification of changes in pain and inflammation responses. Such responses can be determined by identification in changes in the presence of TGF, IL-1 beta and immune cell infiltrate as well as mechanical and thermal sensitivity and physical swelling.

The method of the present invention providing the administration of the antioxidant composition wherein the transdermal formulations overcome several difficult problems inherent in incorporating high concentrations (greater than about 2% w/w) of aqueous-soluble, charged inorganic salts (e.g., strontium salts) into aesthetic (e.g., pleasant-feeling, elegant, etc.) and functionally active topical products (i.e., products which retain their cosmetic, therapeutic, or other functional characteristics).

The method of the present invention providing the administration of the antioxidant composition wherein the composition is contained in the transdermal formulations that are miscible and will remain in solution. Consequently, in accordance with the inventive method, the transdermal formulations can be conveniently applied to the skin in the area of pain and inflammation by spaying or misting, or by any other desired liquid application technique. The application can then be reapplied as needed up to as often as once every 1-3 hours.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

Having illustrated and described the principles of the present invention in a preferred embodiment, it will be apparent to those skilled in the art that the embodiment can be modified in arrangement and detail without departing from such principles. Any and all such embodiments are intended to be included within the scope of the following claims.

What is claimed is:

1. A method for increasing iron uptake of macrophage associated with anticipation of inflammatory pain and redistributing the iron for a formation of red blood cells, the method comprising: (a) transdermal administration of a pharmaceutical composition comprising melatonin, aspirin, IP6 and zinc in effective amounts to enhance iron uptake of the macrophage for transferring to form new red blood cell formation; and (b) application of the pharmaceutical composition once every 1-3 hours.

2. The method of claim 1 further comprises acceptable carriers and include buffers containing ascorbic acid, low molecular weight polypeptides with less than about 10 residues, and hydrophilic polymers.

3. The method of claim 1 wherein transdermal composition is in a form selected from a group consisting of solid, liquid, cream, lotion, spray, gel, and any combination thereof.

4. The method of claim 1 wherein the inflammatory pain associated with iron uptake of macrophage is pain is postherpetic neuralgia, phantom or amputation stump pain, diabetic neuropathy, acquired immune deficiency syndrome neuropathy, back pain, visceral pain, or chronic pancreatitic neuropathy.

\* \* \* \* \*